United States Patent [19]

Atkinson et al.

[11] Patent Number: 4,745,127
[45] Date of Patent: May 17, 1988

[54] BENZYL ESTERS OF BENZOFURAN-2-CARBOXYLIC ACIDS USEFUL AS INHIBITORS OF LEUKOTRIENE BIOSYNTHESIS

[75] Inventors: Joseph G. Atkinson, Montreal; Yvan Guindon, Ile Bizard; Cheuk K. Lau, Pierrefonds, all of Canada

[73] Assignee: Merck Frosst Canada, Inc., Canada

[21] Appl. No.: 1,262

[22] Filed: Jan. 7, 1987

Related U.S. Application Data

[60] Division of Ser. No. 725,265, Apr. 19, 1985, Pat. No. 4,663,347, which is a continuation-in-part of Ser. No. 661,645, Oct. 17, 1984, abandoned, which is a continuation-in-part of Ser. No. 547,508, Oct. 31, 1983, abandoned.

[51] Int. Cl.[4] .................... A61K 31/34; C07D 307/85
[52] U.S. Cl. .................... 514/469; 514/212; 514/320; 514/422; 514/452; 514/454; 514/463; 514/468; 540/480; 540/596; 546/196; 548/525; 549/361; 549/387; 549/433; 549/458; 549/467; 549/468
[58] Field of Search ............. 549/467, 468, 361, 387, 549/433, 458; 540/480, 596; 546/196; 548/525; 514/212, 320, 422, 452, 454, 463, 468, 469

[56] References Cited

U.S. PATENT DOCUMENTS 4,229,467 10/1980 Parker .................... 549/468

*Primary Examiner*—Henry R. Jiles
*Assistant Examiner*—Bernard I. Dentz
*Attorney, Agent, or Firm*—Gabriel Lopez; Hesna J. Pfeiffer

[57] ABSTRACT

Compounds of the Formula I:

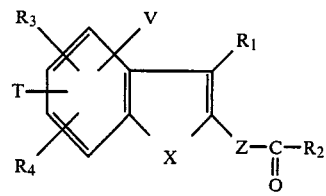

and pharmaceutically acceptable salts thereof are inhibitors of leukotriene biosynthesis. These compounds inhibit the mammalian 5-lipoxygenase enzyme, thus preventing the metabolism of arachidonic acid to the leukotrienes. These compounds are thus useful in the treatment of asthma, allergic disorders, inflammation, skin diseases and certain cardiovascular disorders.

20 Claims, No Drawings

BENZYL ESTERS OF BENZOFURAN-2-CARBOXYLIC ACIDS USEFUL AS INHIBITORS OF LEUKOTRIENE BIOSYNTHESIS

This is a division of application Ser. No. 725,265, filed Apr. 19, 1985, now U.S. Pat. No. 4,663,347, which application is a continuation-in-part of U.S. Ser. No. 661,645, filed Oct. 17, 1984 now abandoned, which is a continuation-in-part of U.S. Ser. No. 547,508, filed Oct. 31, 1983, now abandoned.

This invention is directed to pharmaceutical compositions containing a compound of the Formula I:

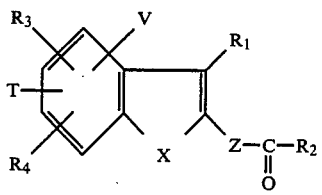

and pharmaceutically acceptable salts thereof wherein the various subtituents are as defined herein below.

This invention also provides a method of treatment for disease states caused by the synthesis of the Leukotrienes $C_4$, $D_4$, $E_4$ and $F_4$, as well as Leukotriene $B_4$, in mammals especially in a human subject. This method comprises administering to said subject an effective amount of a compound of Formula I combined with an appropriate pharmaceutical carrier.

The compounds of Formula I may be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

Finally, this invention also provides novel compounds within the Formula I that act as inhibitors of the mammalian 5-lipoxygenase enzyme system, thus preventing the biosynthesis of the Leukotrienes $C_4$, $D_4$ and $E_4$ and also Leukotriene $B_4$.

U.S. Pat. No. 4,663,347 (Atkinson, et al.,) is incorporated herein by reference in its entirety.

What is claimed is:
1. A compound of the Formula Id:

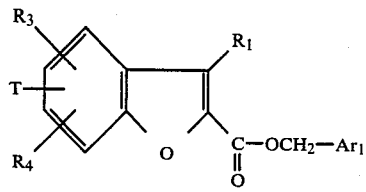

wherein
$R_1$ is hydrogen, $C_1$ to $C_6$ alkyl, $Ar_1$-$C_1$ to $C_3$ alkyl, $Ar_1$ or $CH_2OH$;
$R_3$, $R_4$ and T are each independently selected from:
(1) hydrogen;
(2) alkyl having 1 to 4 carbon atoms;
(3) alkenyl having 2 to 4 carbon atoms;
(4) —$(CH_2)_nM$
wherein n is 0 or 1, and
M is
(a) —$OR_5$;
(b) halogen;
(c) —$CF_3$;
(d) —$SR_5$;
(e) $Ar_1$;
(f) —$COOR_6$;
(g)

wherein $R_{12}$ is H, $C_1$ to $C_6$ alkyl, or $Ar_1$;
(h)

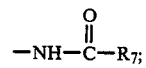

(i)

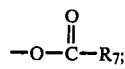

(j)

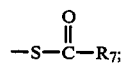

(k)

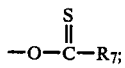

(l) $NR_8R_9$;
(m) —$NHSO_2R_{10}$ wherein $R_{10}$ is $C_1$ to $C_6$ alkyl, phenyl, p-tolyl or $CF_3$;
(n) —$SOR_5$;
(o) —$CONR_8R_9$;
(p) —$SO_2NR_8R_9$;
(q) —$SO_2R_5$;
(r) —$NO_2$; or
(s) —$CN$;
or any two of $R_3$, $R_4$ and T may be joined to form a saturated ring having 5 or 6 ring atoms, said ring atoms comprising 0, 1 or 2 oxygen atoms, the remaining ring atoms being carbon;
each $R_5$ is independently H, $C_1$ to $C_6$ alkyl, benzyl, $Ar_1$, perfluoro-$C_1$-$C_4$ alkyl, $CH_2$-$R_{11}$ wherein $R_{11}$ is $C_1$ to $C_5$ alkyldimethylamino, hydroxy $C_2$ to $C_5$ alkyl, $CH_2COOR_6$, or $CH_2CO$—$R_7$;
each $R_6$ is independently H or $C_1$ to $C_6$ alkyl;
each $R_7$ is indenpendently $C_1$ to $C_6$ alkyl, benzyl, $Ar_1$, $NR_8R_9$, $NHAr_1$, or O—$C_1$ to $C_4$ alkyl;
each $R_8$ and each $R_9$ is independently H or $C_1$ to $C_4$ alkyl, or $R_8$ and $R_9$ may be joined through the N to which they are attached to form a heterocycloalkyl ring having 5 to 8 ring atoms; and
each $Ar_1$ is independently 1- or 2-naphthyl, phenyl or mono- or disubstituted phenyl, wherein the substituents on the phenyl are independently selected from $C_1$ to $C_3$ alkyl, I, Br, Cl, F, COOR$_6$, $(CH_2)_n$—NR$_8$R$_9$ wherein n is 0 to 2, methylenedioxy, $C_1$ to $C_3$ alkoxy, OH, CN, NO$_2$, CF$_3$, $C_1$ to $C_4$ acyl, NR$_8$R$_9$, S—$C_1$ to $C_6$ alkyl, SO—$C_1$ to $C_6$ alkyl, and SO$_2$—$C_1$ to $C_6$ alkyl; with the proviso that at least one of R$_3$, R$_4$ or T is either OR$_5$ or —OCOR$_7$;
or a pharmaceutically acceptable salt thereof.

2. A compound of Formula I

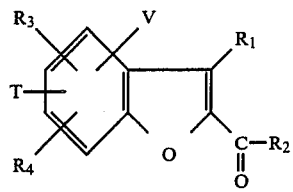

wherein the compound is selected from the following group:

4. A compound of claim 2 which is: 333, 364, 368, or 369.

5. A method of inhibiting mammalian leukotriene biosynthesis or action which comprises administering to a mammal a pharmaceutically effective amount of a compound of claim 2.

6. A method of claim 5 wherein the mammal is a human.

7. A method of treating pulmonary conditions, inflammation, allergies, pain, cardiovascular conditions, or skin conditions which comprises administering to a human in need of such treatment a pharmaceutically effective amount of a compound of claim 2.

8. A pharmaceutical composition useful for inhibiting the biosynthesis of mammalian leukotrienes comprising a pharmaceutically acceptable carrier and an effective amount of a compound of claim 2.

9. A composition of claim 8, wherein the compound is: 223, 224, 232–235, 239, 240, 255, 256, 258, 290, 333, 364, 368, or 369.

| Compound | R$_1$ | R$_2$ | R$_3$ | R$_4$ | T$^c$ |
|---|---|---|---|---|---|
| 223 | CH$_3$ | OCH$_2$Ph—p-OMe | 4-O-C(=O)-OCH$_3$ | H | H |
| 224 | CH$_3$ | OCH$_2$Ph—p-Cl | 4-O-C(=O)-OCH$_3$ | H | H |
| 232 | CH$_3$ | OCH$_2$Ph—3,4-Cl$_2$ | 4-O-C(=O)-OMe | H | H |
| 233 | CH$_3$ | OCH$_2$Ph—3,4-Cl$_2$ | 4-OAc | H | H |
| 234 | CH$_3$ | OCH$_2$Ph | 4-O-C(=O)-OMe | 5-CH$_2$CH=CH$_2$ | H |
| 235 | CH$_3$ | OCH$_2$Ph | 4-O-C(=O)-OPh | H | H |
| 239 | CH$_3$ | OCH$_2$Ph—p-Cl | 4-OAc | H | H |
| 240 | CH$_3$ | OCH$_2$Ph | 4-OAc | H | H |
| 255 | CH$_3$ | O—CH$_2$Ph | 4-OH | H | H |
| 256 | CH$_3$ | OCH$_2$Ph—3,4-Cl$_2$ | 4-OH | H | H |
| 257 | CH$_3$ | OCH$_2$Ph—p-Cl | 4-OH | H | H |
| 258 | CH$_3$ | OCH$_2$Ph—p-OMe | 4-OH | H | H |
| 275 | CH$_3$ | OCH$_2$Ph—p-F | 5-OH | 6-OH | H |
| 276 | CH$_3$ | OCH$_2$Ph—p-Cl | 5-OH | 6-OH | H |
| 277 | CH$_3$ | OCH$_2$Ph—p-OCH$_3$ | 5-OH | 6-OH | H |
| 280 | CH$_3$ | OCH$_2$Ph | 4-OH | 5-CH$_2$SCH$_3$ | H |
| 290 | CH$_3$ | OCH$_2$—Ph—p-OMe | 4-OAc | H | H |
| 292 | CH$_3$ | OCH$_2$Ph | 4-OH | 7-OH | H |
| 293 | CH$_3$ | OCH$_2$Ph | 4-OAc | 7-OAc | H |
| 294 | CH$_3$ | OCH$_2$Ph | 4-OH | 7-OH | 5-CH$_2$CH$_2$CH$_3$ |
| 295 | CH$_3$ | OCH$_2$Ph | 4-OAc | 7-OAc | 5-CH$_2$CH$_2$CH$_3$ |
| 333 | CH$_3$ | OCH$_2$Ph | H | H | $c$ |
| 334 | CH$_3$ | OCH$_2$Ph—p-OMe | H | H | $c$ |
| 335 | CH$_3$ | OCH$_2$Ph—p-Cl | H | H | $c$ |
| 364 | CH$_3$ | OCH$_2$Ph | 5-CH$_2$CH$_2$CH$_3$ | H | $c$ |
| 368 | CH$_3$ | OCH$_2$Ph | 4-OH | 5-CH$_2$CH$_2$CH$_3$ | 7-F |
| 369 | CH$_3$ | OCH$_2$Ph | 4-OH | 5-CH$_2$CH$_2$CH$_3$ | 7-Cl |

$^c$In compounds 223 to 295, V is H; in compounds 333 to 364 T and V are located at positions 4 and 7 respectively and are both simultaneously OH, OCOCH$_3$ or OCO$_2$CH$_3$.

3. A compound of claim 2 which is: 223, 224, 232–235, 239, 240, 255, 256, 258, 290, 333, 364, 368, or 369.

10. A composition of claim 8, wherein the compound is: 255, 333, 364, 368, or 369.

11. A method of inhibiting mammalian leukotriene biosynthesis or action which comprises administering to a mammal pharmaceutically effective amount of a composition of claim 8.

12. A method of claim 11 wherein the mammal is a human.

13. A method of treating pulmonary conditions, inflammation, allergies, pain, cardiovascular conditions, or skin conditions which comprises administering to a human in need of such treatment a pharmaceutically effective amount of a composition of claim 8.

14. A pharmaceutical composition according to claim 8 additionally comprising an effective amount of a second active ingredient selected from the group consisting of non-steriodal anti-inflammatory drugs; peripheral analgesic agents; cyclooxygenase inhibitors; leukotriene antagonists; antihistaminic agents; prostaglandin antagonists; and thromboxane antagonists.

15. A pharmaceutical composition according to claim 14, wherein the second active ingredient is a non-steroidal anti-inflammatory drug.

16. A pharmaceutical composition according to claim 15, wherein said non-steroidal anti-inflammatory drug is indomethacin.

17. A pharmaceutical composition according to claim 8 additionally comprising an effective amount of a second active ingredient selected from the group consisting of non-steriodal anti-inflammatory drugs; peripheral analgesic agents; cyclooxygenase inhibitors; leukotriene antagonists; antihistaminic agents; prostaglandin antagonists; and thromboxane antagonists, wherein the weight ratio of the compound described in claim 8 to said second active ingredient ranges from about 1000:1 to 1:1000.

18. A pharmaceutical composition according to claim 17, wherein the weight ratio ranges from about 200:1 to 1:200.

19. A pharmaceutical composition according to claim 17, wherein the second active ingredient is a non-steroidal anti-inflammatory drug.

20. A pharmaceutical composition according to claim 19, wherein the non-steroidal anti-inflammatory drug is indomethacin.

* * * * *